United States Patent [19]

Wis-Surel et al.

[11] Patent Number: 5,782,933
[45] Date of Patent: Jul. 21, 1998

[54] ASCORBIC AND ISOASCORBIC ACIDS TO REMOVE OR ADJUST OXIDATIVE COLOR IN HAIR

[75] Inventors: Gabriela Wis-Surel, Basingstoke, United Kingdom; Alice Mayer, Bethel; Irina Tsivkin, Stamford, both of Conn.

[73] Assignee: Bristol-Myers Squibb Company, New York, N.Y.

[21] Appl. No.: 846,611

[22] Filed: Apr. 30, 1997

[51] Int. Cl.[6] ........................................... A61K 7/06
[52] U.S. Cl. ........................ 8/431; 8/405; 8/127.6; 8/102; 8/107; 132/202; 132/208
[58] Field of Search ........................... 8/405, 406, 429, 8/431, 432, 127.6, 101, 102, 107; 132/202, 203, 204, 205, 208, 209; 252/188.1, 188.28

[56] References Cited

U.S. PATENT DOCUMENTS

| | | | |
|---|---|---|---|
| 3,337,411 | 8/1967 | Wilmsmann et al. | 8/406 |
| 3,649,158 | 3/1972 | Kalopissis et al. | 8/426 |
| 3,775,044 | 11/1973 | Schrader | 8/435 |
| 5,064,441 | 11/1991 | Kawase et al. | 8/406 |
| 5,224,965 | 7/1993 | Clausen et al. | 8/405 |
| 5,380,340 | 1/1995 | Neunhoeffer et al. | 8/405 |
| 5,480,460 | 1/1996 | Muraoka | 8/405 |

FOREIGN PATENT DOCUMENTS 2657781  8/1991  France.

OTHER PUBLICATIONS

English language translation of FR 2,657,781, L'Oreal, pp. 1–31, Aug. 1991.

*Primary Examiner*—Paul Lieberman
*Assistant Examiner*—Caroline L. Dusheck
*Attorney, Agent, or Firm*—Morton S. Simon

[57] ABSTRACT

Method is provided for reducing the color of dyed hair by contacting the dyed hair with a dilute aqueous composition of ascorbic acid, isoascorbic acid or mixtures and maintaining the contact until the desired reduction is achieved.

6 Claims, No Drawings

# ASCORBIC AND ISOASCORBIC ACIDS TO REMOVE OR ADJUST OXIDATIVE COLOR IN HAIR

BACKGROUND OF INVENTION

This invention is concerned with compositions and methods for altering the color of dyed hair particularly hair that has been dyed with oxidative hair coloring systems. More particularly, it is concerned with compositions containing ascorbic or isoascorbic acid to reduce or remove color in hair, especially human hair, which has been dyed with conventional dye compositions.

Over the last several years, many different dye systems have been defined and these are widely employed to alter the color of human hair. The systems and compositions have been generally classified as permanent, demipermanent and semipermanent. This invention is particularly useful for adjusting or removing permanent hair coloration which has been achieved with oxidative dyes. It will be principally described with reference to such dyes, but the invention is useful with all three classes of dyes.

Oxidative dyeing, known also as permanent hair coloring has been practiced for many years and has several advantages over the other types of coloring systems. It produces a wide range of shades that resist fading and removability by shampoos. The dyes penetrate throughout the hair shaft polymerizing slowly into larger units, thus being more resistant to removal. Once the color deposits in hair, it is relatively resistant to any change either by repetitive washings, light fading or even chemical treatments. The durability of color and its resistance to fading lend oxidative dyeing great popularity. However, there is a segment of hair color users who desire to remove or adjust the artificial color subsequent to its formation.

Oxidative dyeing to achieve permanent hair color is well known to the skilled artisan and need not be described in detail here.

In oxidative dyeing, a mixture of aromatic compounds, generally of the benzenoid series, containing a plurality of nuclear amino and hydroxy functions, and which are themselves colorless, are converted by coupling reactions to a blend of colored compounds within the hair fibers by oxidative processes. The colorless aromatic compounds, in a suitable base formulation, normally are mixed with hydrogen peroxide or other strong oxidizing agent shortly before use. The colored compounds or dyes are, typically, formed by oxidative coupling between primary intermediates (usually diamino benzenes or amino phenols) and couplers which are phenols or related cyclic compounds. Various shades are developed by using a mixture containing more than one of both the intermediate and the coupler.

Because of their low molecular weights and water solubility, the intermediates and couplers diffuse easily into the hair where the coupling reaction takes place. The colored products developed by oxidation, usually with hydrogen peroxide remain trapped in the hair by virtue of their higher molecular weights, relative insolubility in water and absorptive affinity to the internal hair surface.

Demipermanent dyeing is an art recognized form of oxidative dyeing which achieves gray blending rather than a full coverage. A lower volume of hydrogen peroxide together with a milder alkalizer such as monoethanolamine is employed.

Many systems are currently available for reducing or removing color from artificially colored hair. They are based principally on either surfactant solutions, which are not very effective in removing the oxidative colors, or on oxidative systems, such as persulfate based compositions i.e. bleach type products (liquid or powder). The latter are effective in producing slight changes in the artificial hair color but also have serious disadvantages since they also damage hair and to some extent decolorize the natural hair pigment.

One such system is described in French Patent 2,657,781. This system requires an initial oxidation with potassium permanganate followed by treatment with a reducing agent such as sodium bisulfite or hydrosulfite, cysteine, oxalic acid, thioglycolic acid, citric acid or ascorbic acid.

There are also color removing products based on reducing agents such as sodium formaldehyde sulfoxylate (Patent DE 1,151,242, 1963). These products are formulated into two parts; powdery (dry) reducing agent, as one part, and an aqueous composition containing an acid and other additives, as the second part. Both parts must be combined prior to use.

Sodium hydrosulfite is also used in many of the color removers available on the professional market. This compound has to be formulated into a two part system, as described above.

It is a principal object of this invention to provide a facile method for avoiding the difficulties of previous procedures for modifying the color of dyed hair and to provide compositions and kits for achieving this desideratum.

SUMMARY OF THE INVENTION

In accordance with the process of this invention, the color of previously dyed hair, particularly human hair, is reduced or eliminated by contacting the hair with an aqueous composition having a pH of from about 2 to about 5 and containing from about 0.1 percent by weight to about 10 percent by weight of ascorbic or isoascorbic acid. Contact is maintained for a sufficient period of time to achieve the desired reduction, which is, of course, a matter of choice.

In this disclosure and the claims, all percentages are by weight based upon the total weight of the composition.

Because isoascorbic acid appears to be more active at lower concentrations than its isomer, ascorbic acid, it is the preferred hair decolorant. Isoascorbic acid and ascorbic acid are well known in the art. Both acids are relatively strong acids and aqueous compositions containing them are readily prepared at the desired pH level by simply mixing the acid with water in which they are quite soluble. Inert auxiliary solvents such as alcohol or glycerol may be added.

The aqueous solutions may be used as prepared, but it is generally preferred to include in the compositions, surface active agents, thickeners, stabilizers, fragrances, preservatives, sequestering agents and other such components conventionally employed in this art. Buffers may be used to stabilize the pH.

The concentration of the isoascorbic acid or ascorbic acid may vary over a wide range from about 0.1 percent to about 10 percent by weight. Preferred compositions considering economy and efficacy will contain from 0.5 to 5 percent of the selected acid or mixtures thereof.

The compositions are generally employed by applying them to the hair and maintaining contact until the desired effect is achieved. The desired effect is, of course, subjective and a matter of personal preference. The process is applicable to all shades and colors of hair, including black, brown, dark brown, red and blonde. However, with blond hair, the usual purpose of dyeing is to lighten the hair so color reducers will only rarely be used. With the other colors, it is not uncommon for the dyed hair to be darker than that which the user wishes to attain. The compositions employed in this invention are especially useful to such users and they will retain the compositions in contact with the hair until they have achieved the desired result. This may be from about 5 to about 30 minutes but, typically, from about 10 to 20 minutes is preferred. The optimum time will vary with concentration.

Ascorbic acid, also known as vitamin C, as well as other vitamins have been used in cosmetic preparations including compositions for use on hair for various salutory effects. However, they have never been employed in hair preparations at concentrations sufficiently high to achieve the objects of this invention.

The compositions are applied to the hair after the hair has been dyed and the result observed. It is most efficient to apply the compositions shortly after completion of the dyeing process, but the compositions are effective to reduce the original color at any time during the period when the results of the dyeing process are visible, even up to several weeks after the initial color has been produced.

Typically the various ingredients of the compositions will be mixed together and provided for use in one container the volume of which can be made adequate for salon use or for individual use. Alternatively, all of the ingredients except the selected color removing acid can be provided in one container and the acid in a second container. The ingredients of the separate containers can be mixed just prior to use.

Surface active agents may be employed in the compositions of the invention to aid in the solubilization process and to improve the penetration rate of the color reducing acid into the hair follicle.

Surface active agents employed in the compositions of this invention can be anionic, nonionic, cationic or amphoteric provided they are compatible with the system. By way of examples of the various types of surface active agents, there can be mentioned: higher alkylbenzene sulfonates; alkylnaphthalenesulfonates; sulfonated esters of alcohols and polybasic acids; taurates; fatty alcohol sulfates; sulfates of branched chain or secondary alcohols; alkyldimethylbenzylammonium chlorides, salts of fatty acids or fatty acid mixtures; N-oxyalkylated fatty acid alkanolamides, and the like. Illustrative of specific surfactants there can be mentioned: sodium lauryl sulfate; polyoxyethylene lauryl ester; myristyl sulfate; glyceryl monostearate; triethanolamine oleate, sodium salt of palmitic methyl taurine; cetyl pyridinium chloride; lauryl sulfonate; myristyl sulfonate; lauric diethanolamide; polyoxyethylene stearate; ethoxylated oleoyl diethanolamide; polyethylene glycol amides of hydrogenated tallow; stearyldimethyl benzyl ammonium chloride; dodecylbenzene sodium sulfonate; triethanolamine salt of p-dodecylbenzene sulfonate; nonylnaphthalene sodium sulfonate; dioctyl sodium sulfosuccinate; sodium N-methyl-N-oleoyl taurate; oleic acid ester of sodium isothionate; sodium dodecyl sulfate; the sodium salt of 3-diethyl tridecanol-6-sulfate and the like. The quantity of surface active agent can vary over a wide range, such as from about 0.05% to about 15% and preferably from about 0.10 to 5% by weight of the composition.

Because they are readily and economically available, the presently preferred surfactants are polyethylene glycol castor oil, behenic acid, ceteareths, cocamidopropyl betaine, ethyl polyethylene glycol cocamine sulfate nonoxyanol, polyethylene glycol stearate, sulfated castor oil and polyethylene glycol tallow amide.

A thickening agent may also be incorporated in the composition of this invention. It may be one or several of those commonly used in cosmetic compositions. These are exemplified by such products as sodium alginate, gum arabic, cellulose derivatives, such as methylcellulose, e.g., Methocel 60HG, or the sodium salt of carboxymethylcellulose, or hydroxyethylcellulose, e.g., Cellosize QP-40, acrylic polymers, such as polyacrylic acid sodium salt, and inorganic thickeners, such as bentonite. The quantity of this thickening agent can also vary over a wide range, even as high as 20%. Ordinarily it will range from about 0.5 to about 5% by weight of the composition. The viscosity of the composition may vary from about 1 cp to about 100,000 cps. For a typical lotion formulation, composition viscosity is between about 100 cps to about 10,000 cps.

The compositions may also contain other conventional additives such as fragrances, dyes and pigments, which are well known additives that will not affect the hair.

The compositions are preferably liquids, but they may be in the form of emulsions, suspensions, lotions, gels or other forms employed in the cosmetic arts.

The compositions utilized in the practice of the invention can be prepared by conventional methods used in the art. Thus, they can be prepared by dissolving or suspending the components in the selected media with adequate mixing. Preparation may take place at ambient temperatures, i.e., 20° to 35° C., but solubility and rate of preparation can be enhanced utilizing elevated temperatures, for example 40° to 100° C.

The following examples are given by way of illustration only and should not be regarded as in any way limiting the scope of the present invention since many apparent variations are possible without departing from its spirit and scope.

In following examples Hunter Chromaticity values are employed to define the color of the hair. The meanings of these values are well known to those skilled in the art.

In the Hunter Tristimulus System, L is a measure of lightness and darkness, that is, the depth of the color of the hair tress. The lower the value of L, the darker the color.

A decrease in the value of L indicates a darkening of the hair tress.

The a value is a measure of the greenness or redness of the hair's color. As the a value increases, the hair has a more prominent red tonality. A lowering in the value results in greener shades.

The value of b is a measure of the blueness or yellowness of the hair color. As the b value increases, the hair tress is more yellow.

Seven compositions typical of the present invention were prepared by dissolving the selected amount of isoascorbic acid in distilled water. The remaining ingredients (except the hydroxyethyl cellulose) were added thereto together with sufficient water to bring the volume to about 50% of the final volume. The mixture was then heated to form a solution. Cold water, about 25% of the final total volume, was then added to the solution and it was allowed to cool to room temperature. The hydroxyethyl cellulose was then slowly added to the solution at room temperature so as to avoid clumping. The fragrance and sufficient water to bring the composition to final volume were then added.

The amounts are in percent by weight. The compositions were utilized in the examples.

|  | A | B | C | D |
|---|---|---|---|---|
| Isoascorbic acid | 0.1 | 9.25 | 0.5 | 1.0 |
| Oleic acid | 1.0 | 1.0 | 1.0 | 1.0 |
| Aminomethyl propanol (AMP) | 0 | 0 | 0 | 0.05 |
| Hydroxyethyl cellulose | 1.5 | 1.5 | 1.5 | 1.5 |
| PEG-tallow amide | 2.0 | 2.0 | 2.0 | 2.0 |
| Polyglucose (Plantaran 1200) | 1.0 | 1.0 | 1.0 | 1.0 |
| Fragrance | 0.3 | 0.3 | 0.3 | 0.3 |
| Water | 94.1 | 93.95 | 93.7 | 93.15 |
| pH | 4.25 | 3.67 | 3.44 | 3.63 |

|  | E | F | G |
|---|---|---|---|
| Isoascorbic acid | 3.0 | 5.0 | 7.0 |
| Oleic acid | 1.0 | 1.0 | 1.0 |
| Aminomethyl propanol (AMP) | 0.37 | 0.85 | 1.46 |
| Hydroxyethyl cellulose | 1.5 | 1.5 | 1.0 |
| PEG-tallow amide | 2.0 | 2.0 | 2.0 |
| Polyglucose (Plantaran 1200) | 1.0 | 1.0 | 1.0 |
| Fragrance | 0.3 | 0.3 | 0.3 |
| Water | 90.83 | 88.35 | 86.24 |
| pH | 3.56 | 3.49 | 3.5 |

In each of the following examples, a blended gray hair tress was colored with the commercial product indicated and, after the dyeing process was complete, the color was reduced with one of the above compositions or with one of the compositions identified at the head of the appropriate column, for the time periods indicated. The Hunter values before and after decoloring indicate that the compositions of the invention effect substantial decoloration. Each decoloring treatment was conducted at ambient temperature. The hair was then rinsed, dried and evaluated. The decoloring compositions were compared with commercially available decolorizing compositions.

EXAMPLE 1

Semipermanent

Loving Care®—Natural Black

|  | Initial | F 30 min. | G 30 min. | Uncolor ® For Semipermanent 30 min. | Metalex ®/20 vol. Pure White ® Creme Developer 30 min. |
|---|---|---|---|---|---|
| L | 22.28 | 23.18 | 23.13 | 25.01 | 25.04 |
| a | 1.79 | 2.56 | 2.15 | 2.12 | 2.53 |
| b | 4.09 | 4.71 | 4.67 | 3.35 | 4.42 |

EXAMPLE 2

Semipermanent

Loving Care®—Redwood Brown

|  | Initial | F 30 min. | G 30 min. | Uncolor ® For Semipermanent 30 min. | Metalex ®/20 vol. Pure White ® Creme Developer 30 min. |
|---|---|---|---|---|---|
| L | 20.69 | 23.96 | 23.87 | 24.38 | 23.27 |
| a | 8.62 | 9.69 | 9.22 | 8.24 | 9.17 |
| b | 4.52 | 6.23 | 6.11 | 5.52 | 5.57 |

Examples 1 and 2 illustrate that some color is removed with this system and, although the L value change is not as great as with commercial color removers, the hair appears lighter due to the larger b value.

EXAMPLE 3

Demipermanent

Natural Instincts®—Black Cherry

|  | Initial | F 30 min. | G 30 min. | Instant White ®/ Pure White$^R$ Developer 30 min. |
|---|---|---|---|---|
| L | 13.42 | 15.96 | 14.57 | 13.86 |
| a | 2.42 | 2.18 | 2.09 | 2.58 |
| b | 1.64 | 2.79 | 2.41 | 1.47 |

EXAMPLE 4

Demipermanent

Natural Instincts®—Nutmeg

|  | Initial | F 30 min. | G 30 min. | Instant Whip ®/ Pure White ® Developer 30 min. |
|---|---|---|---|---|
| L | 18.46 | 19.42 | 19.80 | 20.29 |
| a | 1.90 | 2.14 | 1.92 | 2.45 |
| b | 4.82 | 5.83 | 5.31 | 5.86 |

Examples 3 and 4 show that the color removal system of this invention is as effective on demipermanent-dyed hair as commercial removers.

EXAMPLE 5

Permanent

Nice 'N Easy®—Natural Tawny Auburn

|  | Initial | F 5 min. | G 10 min. | F 10 min. | 3% isoascorbic acid (in H$_2$O) 10 min. | 5% isoascorbic acid (in H$_2$O) 10 min. |
|---|---|---|---|---|---|---|
| L | 26.71 | 33.84 | 31.11 | 29.58 | 31.23 | 29.17 |
| a | 3.93 | 3.04 | 2.86 | 3.05 | 2.71 | 2.78 |
| b | 5.56 | 7.90 | 7.70 | 7.55 | 7.34 | 7.33 |

EXAMPLE 6

Permanent

Nice 'N Easy®—Natural Tawny Auburn

|  | Initial | 7% isoascorbic acid (in H$_2$O) 10 min. | 0.25% isoascorbic acid (in H$_2$O) 10 min. |
|---|---|---|---|
| L | 27.55 | 30.75 | 27.28 |
| a | 4.54 | 3.47 | 4.15 |
| b | 7.12 | 8.26 | 7.37 |

Examples 5 and 6 show that the system of the invention is equally efficient in water and in simple surfactant based systems. The examples also show that the degree of color removal can be adjusted by modifying the time of exposure as well as the concentration of color removal agents.

EXAMPLE 7

Permanent

Nice 'N Easy®—Natural Tawny Auburn

|   | Initial Initial | 0.5% isoascorbic acid in Herbal Essences ® Moisture Balancing For Normal Hair 30 min. | 0.5% isoascorbic acid in Herbal Essences ® For Normal Hair 30 min. |
|---|---|---|---|
| L | 27.08 | 28.80 | 29.91 |
| a | 3.90  | 2.86  | 3.51  |
| b | 6.42  | 6.38  | 6.78  |

EXAMPLE 8

Permanent

Nice 'N Easy®—Natural Soft Dark Brown

|   | Initial | 0.5% isoascorbic acid in Herbal Essences ® Moisture Balancing For For Normal Hair 30 min. | 0.5% isoascorbic acid in Herbal Essences ® For Normal Hair 30 min. |
|---|---|---|---|
| L | 17.51 | 14.36 | 15.56 |
| a | 1.44  | 1.43  | 1.66  |
| b | 4.43  | 2.62  | 3.61  |

Examples 7 and 8 show that some shampoo bases may contain ingredients that can reduce the effectiveness of color removal.

EXAMPLE 9

Permanent

Nice 'N Easy®—Natural Tawny Auburn

|   | Initial | C 10 min. | D 10 min. | D 10 min. Followed By $H_2O_2$ at pH 9.67 10 min. |
|---|---|---|---|---|
| L | 24.58 | 25.49 | 27.90 | 28.62 |
| a | 4.15  | 3.60  | 3.54  | 3.11  |
| b | 5.78  | 6.02  | 7.00  | 6.62  |

EXAMPLE 10

Permanent

Nice 'N Easy®—Natural Soft Dark Brown

|   | Initial | 7% isoascorbic acid (in $H_2O$) 10 min. | C 10 min. | D 10 min. | D 10 min. Followed By $H_2O_2$ at pH 9.67–10 min. |
|---|---|---|---|---|---|
| L | 16.81 | 19.12 | 18.64 | 17.09 | 18.10 |
| a | 1.64  | 1.80  | 1.48  | 1.5   | 1.50  |
| b | 3.7   | 4.95  | 4.61  | 3.1   | 4.15  |

The results of Examples 9 and 10 show that the color is not reformed by a subsequent oxidative treatment with $H_2O_2$ after color has been removed by the removal system.

EXAMPLE 11

Permanent

Nice 'N Easy®—Natural Soft Dark Brown

|   | Initial | F 10 min. | 5% Ascorbic acid (in $H_2O$) 10 min. | A 10 min. | B 10 min. | A 30 min. |
|---|---|---|---|---|---|---|
| L | 18.98 | 19.49 | 19.68 | 18.34 | 18.92 | 19.99 |
| a | 1.85  | 1.98  | 1.85  | 1.72  | 1.94  | 1.86  |
| b | 4.90  | 5.38  | 5.22  | 4.98  | 5.08  | 5.38  |

This example shows that in some instances lower concentrations of isoascorbic acid may require longer contact times with the hair to be effective.

EXAMPLE 12

Permanent

Nice 'N Easy®—Natural Soft Dark Brown

|   | Initial | F 10 min. | F 5 min. | E 10 min. | 5% isoascorbic acid (in $H_2O$) 10 min. |
|---|---|---|---|---|---|
| L | 17.97 | 19.57 | 18.58 | 20.61 | 19.91 |
| a | 1.63  | 1.74  | 1.72  | 1.60  | 1.82  |
| b | 4.29  | 4.95  | 4.63  | 5.05  | 5.30  |

The results of Examples 11 and 12 show that ascorbic and isoascorbic acid are both effective color removal agents and that the degree of color removal can be adjusted by modifying either the time of contact or the concentration of the components.

What is claimed is:

1. A one step method of reducing the color of dyed human hair which consists essentially of contacting the hair with an aqueous composition consisting essentially of from about 0.1 percent to about 10 percent by weight based on the total weight of the composition of ascorbic acid, isoascorbic acid or mixtures thereof and maintaining such contact for from about 5 to 30 minutes.

2. The method as in claim 1, wherein the composition contains from about 0.5 percent by weight to about 5 percent by weight of isoascorbic acid, ascorbic acid, or a mixture thereof.

3. The method as in claim 2, wherein the composition contains from about 0.5 percent by weight to about 5 percent by weight of ascorbic acid.

4. The method as in claim 1, wherein the contact time is from about 10 to 20 minutes.

5. The method as in claim 2, wherein the contact time is from about 10 to 20 minutes.

6. The method as in claim 2, wherein the contact time is from about 10–20 minutes.

* * * * *